US011607437B2

(12) United States Patent
Park et al.

(10) Patent No.: US 11,607,437 B2
(45) Date of Patent: Mar. 21, 2023

(54) COSMETIC AND PHARMACEUTICAL COMPOSITIONS EACH CONTAINING ALOE EXTRACT AND UPLAND RICE EXTRACT

(71) Applicant: DAEBONG LS, LTD, Incheon (KR)

(72) Inventors: Jin-Oh Park, Seoul (KR); Ji-Won Lee, Seoul (KR); Hye-Ja Lee, Seogwipo-si (KR); Ji-Hye Kim, Seogwipo-si (KR); Won-Bo Oh, Seogwipo-si (KR)

(73) Assignee: DAEBONG LS, LTD, Incheon (KR)

( * ) Notice: Subject to any disclaimer, the term of this patent is extended or adjusted under 35 U.S.C. 154(b) by 0 days.

(21) Appl. No.: 16/649,761

(22) PCT Filed: Oct. 1, 2018

(86) PCT No.: PCT/KR2018/011619
§ 371 (c)(1),
(2) Date: Mar. 23, 2020

(87) PCT Pub. No.: WO2019/066606
PCT Pub. Date: Apr. 4, 2019

(65) Prior Publication Data
US 2020/0237848 A1 Jul. 30, 2020

(30) Foreign Application Priority Data

Sep. 29, 2017 (KR) ........................ 10-2017-0127181

(51) Int. Cl.
*A61K 36/886* (2006.01)
*A61K 8/9794* (2017.01)
*A61K 8/9789* (2017.01)
*A61K 36/28* (2006.01)
*A61K 36/33* (2006.01)
*A61K 36/899* (2006.01)
*A61Q 19/00* (2006.01)

(52) U.S. Cl.
CPC .......... *A61K 36/886* (2013.01); *A61K 8/9789* (2017.08); *A61K 8/9794* (2017.08); *A61K 36/28* (2013.01); *A61K 36/33* (2013.01); *A61K 36/899* (2013.01); *A61Q 19/00* (2013.01)

(58) Field of Classification Search
CPC ..................................................... A61K 36/00
USPC ......................................................... 424/725
See application file for complete search history.

(56) References Cited

U.S. PATENT DOCUMENTS

2015/0342854 A1* 12/2015 Shibuya ................. A61K 8/676
424/62

FOREIGN PATENT DOCUMENTS

| JP | 02011093880 | * | 5/2011 |
| KR | 10-2005-0046464 | * | 5/2005 |
| KR | 10-2012-0101897 A | | 9/2012 |
| KR | 10-2016-0119967 A | | 10/2016 |
| KR | 10-2017-0108470 A | | 9/2017 |
| KR | 10201708470 | * | 9/2017 |
| WO | 2016/017894 A1 | | 2/2016 |
| WO | WO 2016 017894 | * | 2/2016 |

OTHER PUBLICATIONS

Retrieved from the Internet, "Certification Mark for Jeju Cosmetics : Cosmetic Cert JEJU / Visiting UCL Factory", Jul. 20, 2016, <https://blog.naver.com/jhgeel/220766489017> see pp. 6-8.
Internet News Article "LG Household & Health Care Ltd., Launching a Cosmetic Product Officially Certified in Jeju for the First Time", Jun. 2, 2016, <http://www.mainnews.co.kr/news/articleView.html?idxno=11732> see p. 2.
International Search Report issued for PCT/KR2018/011619, dated Jan. 14, 2019.
Written Opinion of the International Searching Authority issued for PCT/KR2018/011619, dated Jan. 14, 2019.
Retrieved from the Internet, "How to make Aloe Vera Rice Kheer", Jun. 30, 2016, <https://web.archive.org/web/20160630125216/https://www.sanjeevkapoor.com/recipe/Aloe-Vera-Rice-Kheer-Turban-Tadka-FoodFood.html>, retrieved on May 20, 2021.
Database BNPD [Online] Mintel; Sep. 30, 2016, anonymous: "First Serum", XP55805490, Database accession No. 4061923.
Database BNPD [Online] Mintel; Sep. 29, 2016, anonymous: "Cream", XP055805497, Database accession No. 4061921.
Garba, U., et al. "Extraction and utilization of rice bran oil: A review" The 4th International Conference on Rice Bran Oil 2017 (ICRBO 2017) Rice Bran Oil Application: Pharma-Cosmetics, Nutraceuticals and Foods Aug. 24-25, 2017, XP055805499, retrieved on May 18, 2021.
Oliveira, R. et al. "Effects of the extraction conditions on the yield and composition of rice bran oil extracted with ethanol: A response surface approach", Food and Bioproducts Processing, Institution of Chemical Engineers, Rugby GB, vol. 90, No. 1, Jan. 13, 2011, pp. 22-31, XP028339814, ISSN: 0960-3085, DOI: 10.1016/J.FBP.2011.01.004, retrieved on Jan. 19, 2011.
Database BNPD [Online] Mintel; Sep. 6, 2017, anonymous: "Intensive Overnight Mask", XP055805299, Database accession No. 5076311.
Search Report issued for European patent application serial No. 18861111.5, dated Jun. 18, 2021.

* cited by examiner

*Primary Examiner* — Michael V Meller
(74) *Attorney, Agent, or Firm* — Westman, Champlin & Koehler, P.A.; Amanda M. Prose

(57) ABSTRACT

The present invention relates to cosmetic and pharmaceutical compositions each containing a composite extract. More specifically, the present invention provides cosmetic and pharmaceutical compositions, each of which contains, as an active ingredient, a composite extract of an aloe extract and an upland rice extract, leading to excellent moisturizing, anti-inflammatory, and atopy alleviating effects, and thus can be favorably used for prevention, alleviation, and treatment of a skin disease.

1 Claim, 1 Drawing Sheet

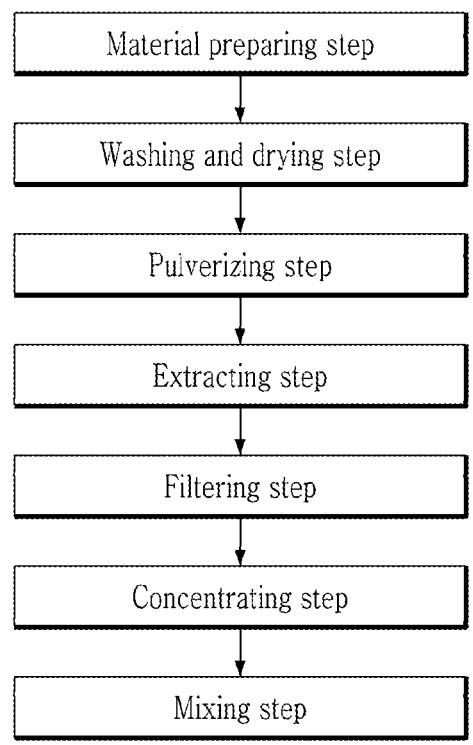

COSMETIC AND PHARMACEUTICAL COMPOSITIONS EACH CONTAINING ALOE EXTRACT AND UPLAND RICE EXTRACT

CROSS-REFERENCE TO RELATED APPLICATION

This Application is a Section 371 National Stage Application of International Application No. PCT/KR2018/011619, filed Oct. 1, 2018 and published as WO 2019/066606 A1 on Apr. 4, 2019, which claims priority to KR 10-2017-0127181, filed Sep. 29, 2017, the contents of which are hereby incorporated by reference in their entirety.

TECHNICAL FIELD

The present disclosure relates to cosmetic and pharmaceutical compositions comprising a composite extract and, more specifically, to cosmetic and pharmaceutical compositions which can be usefully used for prevention, alleviation and treatment of skin diseases by comprising a composite extract, as an active ingredient, of an aloe extract and an upland rice extract.

BACKGROUND ART

Skin plays important roles of transporting about 65 to 70% of moisture possessed by the human body, i.e., various bioactive substances required in the human body, and adjusting evaporation of moisture helping the skin maintain a soft and moist state to exterior of the body.

Such skin is mainly classified into three layers of epidermis, corium and subcutaneous fatty tissue. Particularly, epidermis positioned on an outermost region of the skin performs a protection function of blocking excessive penetration of material from the outside and suppressing excessive evaporation of moisture to the exterior of the body.

Such a protection function can be main by normally forming and maintaining stratum corneum formed of keratinocytes.

The keratinocytes are cells which have been formed by passing through shape and functional changes in stages while basal cells that has been consistently proliferated in stratum basale are being moved to stratum corneum, and an epidermis differentiation or keratinization process in which old keratinocytes are separated from the skin after a certain period of time, and new keratinocytes risen up from the stratum basale perform functions of the old keratinocytes is repeated. The keratinocytes in such a keratinization process not only acts to exhibit softness of the skin, but also enables appropriate moisture to be maintained by producing a high concentration natural moisturizing factor (NMF), i.e., a water-soluble component, and intercellular lipids such as ceramide, cholesterol, and fatty acid, ands allowing the stratum corneum to function as a blocking layer from the outside, thereby retaining a function as a skin barrier.

Due to a variety of causes including artificial temperature control of air conditioning and heating caused by an environmental change or a change of lifestyle, various stresses produced from social life and skin stress caused by environmental pollution, frequent face washing according to makeup habit, natural skin aging caused by age increase, etc., xeroderma regarded as one of main diseases of modern society, as one of symptoms caused by functional abnormality of a skin barrier, has been increasing a need for a skin moisturizer by generating phenomena that moisture of stratum corneum is reduced to make the skin dry and the surface of the skin rough, and the skin loses gloss such that the skin is looked to be dull.

Further, an atopic dermatitis occurring in 10% of young children has also been known to be caused by main causes such as xeroderma, more basically functional abnormality of the skin barrier.

In order to treat such an atopic dermatitis, many researches for supplying moisture from the outside or minimizing loss of moisture from the interior of the body by placing emphasis on maintenance of appropriate moisture in the skin have conventionally been progressed, and a humectant such as ceramide or derivatives thereof having moisture holding ability has actually been developed and has frequently been used in a pharmaceutical or cosmetic area.

Polyvalent alcohols such as glycerin, propylene glycol, sorbitol, etc. as a humectant has conventionally been used the most, and although sodium hyaluronate by microorganisms has also been used, sodium hyaluronate may cause a bad influence on the skin by occurrence of asteatosis, irritation, allergy, etc. due to use of chemical raw materials.

In order to complement this, it is urgent to develop natural eco-friendly natural ingredients which is safe to a human body, and has, above all things, activities of enhancing skin elasticity, improving anti-inflammation, alleviating atopy, and improving skin moisture and skin texture.

DISCLOSURE

Technical Problem

The present invention has been devised to solve the above-mentioned problem, and an objective of the present disclosure is to provide cosmetic and pharmaceutical compositions which can be usefully used for prevention, alleviation and treatment of skin diseases by comprising a composite extract, as an active ingredient, including an aloe extract and an upland rice extract.

Technical Solution

A cosmetic composition according to an aspect of the present invention comprises a composite extract, as an active ingredient, including an aloe extract and an upland rice extract.

The composite extract may include 10 to 300 parts by weight of the upland rice extract with respect to 100 parts by weight of the aloe extract.

The composite extract may additionally include at least one extract selected from the group consisting of an *Opuntia humifusa* extract, an *Echinacea purpurea* extract, and a glutinous foxtail millet extract.

The composite extract may include at least one extract selected from the group consisting of 10 to 300 parts by weight of an *Opuntia humifusa* extract, 10 to 300 parts by weight of an *Echinacea purpurea* extract, and 10 to 300 parts by weight of a glutinous foxtail millet extract with respect to 100 parts by weight of the aloe extract.

The aloe extract, upland rice extract, *Opuntia humifusa* extract, *Echinacea purpurea* extract and glutinous foxtail millet extract may be extracted by using 30 to 70% ethanol as a solvent.

The cosmetic composition may be used for moisturization, anti-inflammation, or atopy alleviation.

The cosmetic composition may have a formulation selected from the group consisting of tonic, emulsion, gel, cream, lotion, essence, foam, pack, soap, ointment, spray, and powder.

A pharmaceutical composition according to the other aspect of the present invention comprises the composite extract as an active ingredient.

The pharmaceutical composition may be used for prevention, alleviation or treatment of atopy.

Advantageous Effects

Cosmetic and pharmaceutical compositions comprising a composite extract, as an active ingredient, including an aloe extract and an upland rice extract according to the present invention can be usefully used for prevention, alleviation or treatment of skin diseases since the cosmetic and pharmaceutical compositions are excellent in a moisturizing effect, an anti-inflammatory effect, and an atopy alleviating effect.

DESCRIPTION OF DRAWING

FIG. 1 is a flow chart illustrating an obtainment process for obtaining a composite extract of the present invention.

MODE FOR INVENTION

Hereinafter, embodiments of the present invention will be described in detail. However, these embodiments are only exemplary, and the present invention is not limited thereto, and will only be defined by the scope of the claims to be described later.

If, in the description of the present invention, detailed descriptions of well-known functions or configurations may unnecessarily make the gist of the present invention obscure, the detailed descriptions will be omitted.

In describing the elements of the present invention, the terms of a first, a second, A, B, (a), (b), or the like, can be used. Such terms are used for merely discriminating the corresponding elements from other elements and the corresponding elements are not limited in their inherent characteristics, order, or sequence by the terms.

In the present invention, an extract includes all extracts, fractions and purified materials, and diluted solutions, concentrates or dried materials thereof obtained from each step of extraction, fractionation or purification.

In the present invention, term 'prevention', 'alleviation' or 'treatment' means suppression, reduction or removal of appearance or development for one or more symptoms associated with disease or illness.

When unique manufacture and material allowable errors of numerical values are suggested to mentioned meanings of terms in the present invention such as "about", "substantially", "extent", etc., the terms are used as a meaning of the numerical values or a meaning near the numerical values, and the terms are used to prevent that an unscrupulous infringer unfairly uses a disclosure content in which exact or absolute numerical values are mentioned to help understanding of the present invention.

A cosmetic composition according to an embodiment of the present invention may comprise a composite extract, as an active ingredient, including an aloe extract and an upland rice extract.

The composite extract may include 10 to 300 parts by weight, preferably 20 to 200 parts by weight of the upland rice extract with respect to 100 parts by weight of the aloe extract. There may be a problem that the cosmetic composition may have an insignificant efficacy or effect when the composite extract includes less than 10 parts by weight of the upland rice extract with respect to 100 parts by weight of the aloe extract, while there may be an economic problem since the cosmetic composition is inefficient in improvement of efficacy or effect compared to a used amount when the composite extract includes more than 300 parts by weight of the upland rice extract with respect to 100 parts by weight of the aloe extract.

Although aloe, as a succulent perennial herb which has been nowadays used as a world-wide medicinal plant, is similar to cactus in appearance, aloe actually belongs to aloe genus of lily family, and occupies about one tenth of lily family. Aloe native to area of a warm, dry climate, which had been used in treatment of wound, burn and inflammation of the skin by ancient Egyptians. In recent times of early 1930s, aloe had been frequently used in treatment of a mild skin disease or radiation dermatitis by hospitals. Due to its wound healing effects, aloe has been loved by many people since the time of Greece when there was no medical history, and aloe has been used as a skin beauty care ingredient for a long time since ancient times.

Although there are somewhat differences according to types of aloe, aloe has a spear-like shape, thorns are formed in both ends of green leaves, and ends of the leaves are sharp. Aloe comprises, as main ingredients, hexose-containing high molecule polysaccharides, aloetin, aloe ulcin, alomicin, etc., and these ingredients mostly exist in a gel which is inside the leaves.

Aloe has widely been known as a plant supplying moisture to the skin, particularly makes a moisture protection film on the delicate baby skin by having an excellent skin moisturizing effect. Further, aloe exhibits excellent effects also in wound healing and cell regeneration, and aloetin, a main ingredient of aloe, exhibits an excellent effect in prevention of skin troubles by having an effect in skin disinfection.

The aloe extract may be obtained by using ethanol as an extraction solvent, and may be obtained by drying aloe, pulverizing the dried aloe, and extracting the aloe powder by using 30 to 70% ethanol as the extraction solvent.

Upland rice, as rice cultivated in a field, has characteristics of enduring draught as upland rice is grown well in a non-irrigated field state differently from aquatic rice cultivated in an irrigated rice paddy during a whole growth period. A report for aquatic rice and upland rice which was published in Rural Development Administration diversely describes differences between aquatic rice and upland rice.

The differences between aquatic rice and upland rice in the report will be described below in brief. It is described in the report that, with regard to a production increase suppressing function, as leaves become somewhat thicker, the number of pores is reduced, and an opening and closing function of opening and closing the pores becomes susceptible in upland rice compared to aquatic rice, upland rice has an advantage of high moisture storage capacity by having thick and large leaves compared to aquatic rice, and upland rice having thick stems and large vessels in addition to thick roots with a deep-dwelling disposition is related to moisture supply capacity of upland rice itself. Further, it is described in the report that upland rice has high resistance to potassium chlorate ($KClO_3$) compared to aquatic rice, and particularly, an upland rice variety having a high drought-resistant power during young rice seedling among upland rice varieties has high resistance to potassium chlorate.

As there are various differences between upland rice and aquatic rice due to varietal improvement, it is determined that there will also be a difference between moisturizing effects for upland rice and aquatic rice accordingly. Meanwhile, although the upland rice may include upland rice which is native to Jeju-do Province and has been harvested therein, the present invention is not restricted thereby or limited thereto.

The upland rice extract may be obtained by using ethanol as an extraction solvent, and may be obtained by drying upland rice, pulverizing the dried upland rice, and extracting the upland rice powder by using 30 to 70% ethanol as the extraction solvent.

The composite extract including the aloe extract and the upland rice extract may additionally include at least one extract selected from the group consisting of an *Opuntia humifusa* extract, an *Echinacea purpurea* extract, and a glutinous foxtail millet extract.

*Opuntia humifusa*, as a plant belonging to *Opuntia* genus in Cactaceae, is an unique indigenous cactus species which is called as *Opuntia ficusindica* var saboten and grown naturally in Republic of Korea. *Opuntia humifusa*, a wild plant of Jeju-do Province, was designated as Jeju-do Province's monument No. 35 in 1976, is widely cultivated at a place where it is difficult to perform land reclamation as it is grown well in relatively barren soil. Fruits of *Opuntia humifusa* contain very rich dietary fiber, but has a very low calorific value, and comprise 85% of water, 10 to 15% of carbohydrate, 6 to 8% of glucose and fructose, vitamin, and others as main ingredients. Therefore, the fruits of *Opuntia humifusa* have effects including treatment of constipation, a diuretic effect, activation of intestinal motion, improvement of appetite, etc., and are used in treatment of skin diseases, etc.

Although the *Opuntia humifusa* extract may be obtained without limitation from all regions of the plant including fruits, roots, stems, leaves, and others of *Opuntia humifusa*, specifically, the *Opuntia humifusa* extract may be obtained from the fruits of *Opuntia humifusa*.

The *Opuntia humifusa* extract may be obtained by using ethanol as an extraction solvent, and may be obtained by drying *Opuntia humifusa*, pulverizing the dried *Opuntia humifusa*, and extracting the *Opuntia humifusa* powder by using 30 to 70% ethanol as the extraction solvent.

The composite extract may additionally include 10 to 300 parts by weight, preferably 20 to 250 parts by weight of the *Opuntia humifusa* extract with respect to 100 parts by weight of the aloe extract. There may be a problem that the cosmetic composition may have an insignificant efficacy or effect when the composite extract includes less than 10 parts by weight of the *Opuntia humifusa* extract with respect to 100 parts by weight of the aloe extract, while there may be an economic problem since the cosmetic composition is inefficient in improvement of efficacy or effect compared to a used amount when the composite extract includes more than 300 parts by weight of the *Opuntia humifusa* extract with respect to 100 parts by weight of the aloe extract.

*Echinacea purpurea*, as a perennial herbaceous plant of compositae, is native to North America, and is grown to a size of about 60 to 150 cm. *Echinacea purpurea* has a name called as coneflower as an arrangement of small floral leaves, and a protruded center of *Echinacea purpurea* is surrounded by flowers as in daisy. Long oval-shaped *Echinacea purpurea* leaves have a length of 4 to 10 cm and a width of 2 to 4 cm, and have sawteeth formed in edges thereof. Magenta flowers with a diameter of about 10 cm open at ends of stems or branches through June and September. *Echinacea purpurea* has been widely cultivated for ornamental purpose across the world since the flowers of *Echinacea purpurea* are gorgeous, and *Echinacea purpurea* has been used as cold remedies, wound remedies, and others in North America and Europe since *Echinacea purpurea* is excellent in immunity-boosting and anti-inflammation effects.

The *Echinacea purpurea* extract may be obtained by using ethanol as an extraction solvent, and may be obtained by drying *Echinacea purpurea*, pulverizing the dried *Echinacea purpurea*, and extracting the *Echinacea purpurea* powder by using 30 to 70% ethanol as the extraction solvent.

The composite extract may additionally include 10 to 300 parts by weight, preferably 20 to 200 parts by weight of the *Echinacea purpurea* extract with respect to 100 parts by weight of the aloe extract. There may be a problem that the cosmetic composition may have an insignificant efficacy or effect when the composite extract includes less than 10 parts by weight of the *Echinacea purpurea* extract with respect to 100 parts by weight of the aloe extract, while there may be an economic problem since the cosmetic composition is inefficient in improvement of efficacy or effect compared to a used amount when the composite extract includes more than 300 parts by weight of the *Echinacea purpurea* extract with respect to 100 parts by weight of the aloe extract.

It is said that glutinous foxtail millet which is a type of millet, as a crop which has been cultivated for a long time since prehistoric times in all parts of the temperate regions of Asia, has been introduced from China before the introduction of rice. Glutinous foxtail millet has a scientific name of *Setaria italica* Beauvois, and is one of fiver grains. Glutinous foxtail millet has the smallest seed and strong storage properties among the grains. Although there are many types of millet, the millet may be largely divided into glutinous foxtail millet which is glutinous when it steamed and nonglutinous millet which is not glutinous when it steamed. Nutritive components of milled millet comprises about 10% of protein in which prolamin and glutelin are each half-contained, wherein prolamin comprises a small amount of lysine and a large amount of leucine. Glucide is included in an amount of about 70% in the milled millet, and is mostly starch, wherein shape of the starch is similar to starch of rice. Other ingredients of the milled millet may include water, lipid, cellulose, ash, etc. Glutinous foxtail millet has been mainly used when making boiled rice or rice cake by mixing rice with glutinous foxtail millet, or has been used as raw material for confectionery, starch syrup, soju, etc. It is said in traditional Oriental medicine that glutinous foxtail millet not only allows recovery after childbirth and hematopoiesis to be promptly made, but also is good in diabetes and anemia by managing heat and benefiting large intestine.

The glutinous foxtail millet extract may be obtained by using ethanol as an extraction solvent, and may be obtained by drying glutinous foxtail millet, pulverizing the dried glutinous foxtail millet, and extracting the glutinous foxtail millet powder by using 30 to 70% ethanol as the extraction solvent.

The composite extract may additionally include 10 to 300 parts by weight, preferably 20 to 200 parts by weight of the glutinous foxtail millet extract with respect to 100 parts by weight of the aloe extract. There may be a problem that the cosmetic composition may have an insignificant efficacy or effect when the composite extract includes less than 10 parts by weight of the glutinous foxtail millet extract with respect to 100 parts by weight of the aloe extract, while there may be an economic problem since the cosmetic composition is inefficient in improvement of efficacy or effect compared to a used amount when the composite extract includes more than 300 parts by weight of the glutinous foxtail millet extract with respect to 100 parts by weight of the aloe extract.

On the other hand, although the composite extract may be manufactured by obtaining each of the aloe extract, upland rice extract, *Opuntia humifusa* extract, *Echinacea purpurea* extract and glutinous foxtail millet extract, and mixing the extracts according to the above-mentioned mixing ratios, the composite extract may be obtained by extracting the mixed powders by using 30 to 70% ethanol as the extraction solvent after mixing the powders of the aloe, upland rice, *Opuntia humifusa, Echinacea purpurea* and glutinous foxtail millet according to the above-mentioned mixing ratios.

In the present invention, the aloe extract, upland rice extract, *Opuntia humifusa* extract, *Echinacea purpurea* extract and glutinous foxtail millet extract includes all extracts, fractions and purified materials, and diluted solutions, concentrates or dried materials thereof obtained from each step of extraction, fractionation or purification.

In the present invention, the composite extract includes both a mixture including an aloe extract and an upland rice extract, and a mixture in which at least one of an *Opuntia humifusa* extract, an *Echinacea purpurea* extract and a glutinous foxtail millet extract is additionally included in the mixture.

In the present invention, a cosmetic composition comprising the composite extract as an active ingredient may be used for moisturization, anti-inflammation, or atopy alleviation.

In the present invention, the cosmetic composition contains a cosmetologically or dermatologically allowable acceptable medium or base. Although the cosmetic composition may be formulated into all formulations suitable for topical application, e.g., one selected from the group consisting of tonic, emulsion, gel, cream, lotion, essence, foam, pack, soap, ointment, spray, and powder, the present invention is not limited thereto.

In the present invention, the cosmetic composition may comprise ingredients commonly used in the cosmetic composition in addition to the composite extract. For example, the cosmetic composition may comprise supplemental agents commonly used in a cosmetological or dermatological field such as a fat material, an organic solvent, a dissolvent, a thickener, a gelling agent, a softener, an antioxidant, a suspending agent, a stabilizing agent, a foaming agent, an air freshener, a surfactant, water, an ionic or nonionic emulsifier, a filler, a sequestering agent, a chelating agent, a preservative, vitamin, a blocking agent, a wetting agent, essential oil, dye, pigment, a hydrophilic or lipophilic activator, lipid vesicle, or any other ingredients commonly used in cosmetic products. The supplemental agents are introduced in amounts generally used in the cosmetological or dermatological field.

The composite extract as the active ingredient is included in an amount of 0.001 to 20 wt %, preferably 0.05 to 10 wt % in the cosmetic composition based on the total weight of the cosmetic composition. There may be a problem that the cosmetic composition may have an insignificant efficacy or effect when the composite extract is included in an amount of less than 0.001 wt %, while there may be a problem in stability of the formulation when the composite extract is included in an amount of more than 20 wt %.

A pharmaceutical composition according to other embodiment of the present invention may comprise the composite extract as an active ingredient. The pharmaceutical composition may be used for prevention, alleviation or treatment of atopy. The pharmaceutical composition may further comprise pharmaceutical supplemental agents such as a preservative, a stabilizing agent, a hydrating agent or an emulsification accelerator, a salt and/or a buffer for controlling osmotic pressure, etc., and other therapeutically effective substances. The pharmaceutical composition may be formulated into lotion, cream, ointment, gel or the like, the present invention is not limited thereto.

The composite extract as the active ingredient is included in an amount of 0.001 to 20 wt %, preferably 0.05 to 10 wt % in the pharmaceutical composition based on the total weight of the pharmaceutical composition. There may be a problem that the pharmaceutical composition may have an insignificant efficacy or effect when the composite extract is included in an amount of less than 0.001 wt %, while there may be a problem in stability of the formulation when the composite extract is included in an amount of more than 20 wt %.

Hereinafter, the present invention will be additionally described through Preparation Examples and Test Examples. These Examples are provided to elucidate the present invention more specifically, and the scope of the present invention is not limited to these Examples.

EXAMPLES

[Preparation Example 1] Preparing Individual Extracts

After washing each of aloe, Jeju-do Province's upland rice, *Opuntia humifusa* fruit, *Echinacea purpurea* and Jeju-do Province's glutinous foxtail millet with distilled water, fine powder samples were obtained by drying the washed aloe, Jeju-do Province's upland rice, *Opuntia humifusa* fruit, *Echinacea purpurea* and Jeju-do Province's glutinous foxtail millet, and grinding the dried aloe, Jeju-do Province's upland rice, *Opuntia humifusa* fruit, *Echinacea purpurea* and Jeju-do Province's glutinous foxtail millet. Extracts of aloe, Jeju-do Province's upland rice, *Opuntia humifusa*, *Echinacea purpurea* and Jeju-do Province's glutinous foxtail millet were each prepared by mixing purified water with ethanol at a ratio of 5:5 to prepare a solvent, adding the solvent to each of the fine powder samples in a volume amount of about 10 times the fine powder sample, and performing an extraction process two times. After performing the extraction process, and filtering extracted materials with a 400 mesh filter cloth to obtain filtrates, and concentrating the obtained filtrates to a concentration of 50% by using a vacuum evaporator to prepare an aloe extract, a Jeju-do Province's upland rice extract, an *Opuntia humifusa* extract, an *Echinacea purpurea* extract and a Jeju-do Province's glutinous foxtail millet extract of Comparative Examples 1 to 5 as shown in Table 1 below, the prepared aloe extract, Jeju-do Province's upland rice extract, *Opuntia humifusa* extract, *Echinacea purpurea* extract and Jeju-do Province's glutinous foxtail millet extract were used in tests.

[Preparation Example 2] Preparing Composite Extracts 1

After mixing each of the aloe extract, Jeju-do Province's upland rice extract, *Opuntia humifusa* extract, *Echinacea purpurea* extract and Jeju-do Province's glutinous foxtail millet extract prepared in the above-mentioned Preparation Example 1 as in Examples 1 to 9 of the following Table 1 to prepare composite extracts 1, the prepared composite extracts 1 were used in the tests.

[Preparation Example 3] Preparing a Composite Extract 2

After mixing the fine powders of aloe, Jeju-do Province's upland rice, *Opuntia humifusa*, *Echinacea purpurea* and Jeju-do Province's glutinous foxtail millet obtained in the process of the above-mentioned Preparation Example 1 as in Example 10 of the following Table 1 to obtain a fine powder sample, mixing purified water with ethanol at a ratio of 5:5 to prepare a solvent, adding the solvent to the fine powder sample in a volume amount of about 10 times the fine powder sample, and performing an extraction process two times. After performing the extraction process, and filtering an extracted material with a 400-mesh filter cloth to obtain a filtrate, and concentrating the obtained filtrate to a concentration of 50% by using a vacuum evaporator to prepare a composite extract 2 of Example 10, the prepared composite extract 2 was used in the tests.

TABLE 1

| | Aloe extract | Upland rice extract | *Opuntia humifusa* extract | *Echinacea purpurea* extract | Glutinous foxtail millet extract |
|---|---|---|---|---|---|
| Comparative Example 1 | 1 | — | — | — | — |
| Comparative Example 2 | — | 1 | — | — | — |
| Comparative Example 3 | — | — | 1 | — | — |
| Comparative Example 4 | — | — | — | 1 | — |
| Comparative Example 5 | — | — | — | — | 1 |
| Example 1 | 0.5 | 0.5 | — | — | — |
| Example 2 | 0.34 | 0.33 | 0.33 | — | — |
| Example 3 | 0.65 | 0.15 | — | 0.1 | 0.1 |
| Example 4 | 0.2 | 0.1 | — | 0.1 | 0.6 |
| Example 5 | 0.25 | 0.25 | 0.25 | — | 0.25 |
| Example 6 | 0.25 | 0.5 | 0.1 | — | 0.15 |
| Example 7 | 0.25 | 0.25 | 0.25 | 0.25 | — |
| Example 8 | 0.25 | 0.1 | 0.55 | 0.1 | — |
| Example 9 | 0.2 | 0.2 | 0.2 | 0.2 | 0.2 |
| Example 10 | 0.2 | 0.2 | 0.2 | 0.2 | 0.2 |

(Unit: weight ratio)

Test Examples

[Test Example 1] Culturing Skin Keratinocytes and Macrophagocytes

Culturing Skin Keratinocytes

After receiving HaCaT cells, i.e., keratinocytes of skin from Dr. C. G. Hyun (Jeju National University, Korea), the HaCaT cells were cultured at a 37° C. and 5% $CO_2$ pyrostat by using a Dulbecco's Modified Eagle's Medium (DMEM) medium containing 100 units/ml penicillin-streptomycin and 10% fetal bovine serum (FBS), and a successive culture process was performed at intervals of 3 to 4 days.

Culturing Macrophagocytes

After receiving Raw 264.7 cells, i.e., mouse macrophagocytes from American Type Culture Collection (ATCC, USA), the Raw 264.7 cells were used in an experiment. The Raw 264.7 cells were cultured in a 37° C. and 5% $CO_2$ incubator by using a DMEM (Gibco) to which 10% FBS (Gibco) and 1% antibiotic-antimycotic (Gibco) were added, and a successive culture process was performed at intervals of 3 to 4 days.

[Test Example 2] Confirming Cytotoxicity from Skin Keratinocytes and Macrophagocytes An MTT analysis method, as a representative method of measuring cell viability values, comprises allowing live cells with vigorous metabolism to form non-aqueous formazan tinged with purple by reducing aqueous yellow 3-(4,5-dimethylthiazol-2-yl)-2,5-diphenyltetrazolium bromide (MTT) through the action of mitochondrial dehydrogenase within the cells.

In order to confirm cytotoxicity in skin keratinocytes, after putting HaCaT keratinocyte into a 96-well plate in an amount of $3.0 \times 10^5$ cells/mL by using a 10% FBS-added DMEM medium, culturing the HaCaT keratinocyte put into the 96-well plate for 18 hours, and replacing the 10% FBS-added DMEM medium with a serum-free DMEM, extracts to be evaluated were treated in the serum-free DMEM. After adding 50 µl of an MTT solution to the treated extracts, the MTT solution was reacted with the treated extracts for 4 hours. After completely removing a culture medium and adding 200 µl of dimethylsulfoxide (DMSO) to reaction products to completely dissolve precipitates, 540 nm absorbance values of samples were measured by using a microplate reader. Average absorbance values for each sample groups were obtained, and cell growth rates were evaluated by comparing the average absorbance values of the sample groups with an absorbance value of a control group.

In order to confirm cytotoxicity in macrophagocytes, after putting RAW264.7 into a 96-well plate in an amount of $3.0 \times 10^5$ cells/mL by using a 10% FBS-added DMEM medium, culturing the RAW264.7 put into the 96-well plate for 18 hours, and replacing the 10% FBS-added DMEM medium with a DMEM, extracts to be evaluated were treated in the DMEM. After adding 50 µl of an MTT solution to the treated extracts, the MTT solution was reacted with the treated extracts for 4 hours. After completely removing a culture medium and adding 200 µl of dimethylsulfoxide (DMSO) to reaction products to completely dissolve precipitates, 540 nm absorbance values of samples were measured by using a microplate reader. Average absorbance values for each sample groups were obtained, and cell growth rates were evaluated by comparing the average absorbance values of the sample groups with an absorbance value of a control group.

TABLE 2

| | Treatment concentration (µg/mL) | HaCaT cell growth rate (%) | RAW264.7 cell growth rate (%) |
|---|---|---|---|
| Untreated group | — | 100 | 100 |
| Comparative Example 1 | 100 | 106 ± 2.3 | 103 ± 3.9 |
| Comparative Example 2 | 100 | 110 ± 1.4 | 107 ± 1.1 |
| Comparative Example 3 | 100 | 101 ± 3.6 | 102 ± 2.3 |
| Comparative Example 4 | 100 | 105 ± 3.3 | 103 ± 2.1 |
| Comparative Example 5 | 100 | 103 ± 1.8 | 102 ± 1.8 |
| Example 1 | 100 | 106 ± 0.5 | 107 ± 1.7 |
| Example 2 | 100 | 104 ± 1.2 | 106 ± 2.9 |
| Example 3 | 100 | 101 ± 3.6 | 104 ± 2.6 |
| Example 4 | 100 | 104 ± 0.9 | 102 ± 2.3 |
| Example 5 | 100 | 104 ± 1.2 | 105 ± 2.5 |
| Example 6 | 100 | 105 ± 2.1 | 103 ± 2.7 |
| Example 7 | 100 | 106 ± 1.7 | 104 ± 3.2 |
| Example 8 | 100 | 107 ± 0.8 | 103 ± 1.1 |
| Example 9 | 100 | 105 ± 1.1 | 104 ± 1.3 |
| Example 10 | 100 | 102 ± 1.2 | 105 ± 1.2 |

As shown in the above-mentioned Table 2, cytotoxicity values have not been observed from skin keratinocytes in both Comparative Examples 1 to 5, i.e., individual extracts and Examples 1 to 10, i.e., composite extracts.

[Test Example 3] Moisturizing Effects

[Test Example 3-1] Confirming an Effect of Increasing Hyaluronic Acid Production Amount, i.e., Moisturizing Factor After putting HaCaT cells into a 24-well plate, the HaCaT cells were attached to the 24-well plate for 18 hours. After replacing the 24-well plate with a serum-free DMEM, extracts prepared by above-mentioned Table 1 were treated in the serum-free DMEM. After treating samples for 24 hours to collect a culture medium, centrifuging the culture medium at 15,000×rpm for 5 minutes, and collecting a supernatant from the centrifuged material, the collected supernatant was stored at −20° C. until the supernatant was quantified. Hyaluronic acid ELISA kit (Elabscience Biotechnology Co., Ltd) was used in enzyme-linked immunosorbant assay (ELISA), the ELISA was progressed by a method provided by a manufacturer.

TABLE 3

|  | Treatment concentration (μg/mL) | Hyaluronic acid production amount (%) |
|---|---|---|
| Untreated group | — | 100 |
| Comparative Example 1 | 100 | 180 ± 3.2 |
| Comparative Example 2 | 100 | 120 ± 2.8 |
| Comparative Example 3 | 100 | 135 ± 5.1 |
| Comparative Example 4 | 100 | 120 ± 3.2 |
| Comparative Example 5 | 100 | 115 ± 1.2 |
| Example 1 | 100 | 215 ± 2.2 |
| Example 2 | 100 | 225 ± 2.6 |
| Example 8 | 100 | 248 ± 2.3 |
| Example 9 | 100 | 255 ± 2.1 |
| Example 10 | 100 | 260 ± 4.2 |
| Retinoic acid | 10 | 250 ± 0.6 |

As shown in the above-mentioned Table 3, a hyaluronic acid production amount, i.e., a moisturizing factor is higher in the groups treated with the individual extracts of Comparative Examples 1 to 5 and the composite extracts of Examples 1, 2, and 8 to 10 than the untreated group. Particularly, the hyaluronic acid production amount is not less than 255 to 260 in the composite extracts of Examples 9 and 10 including aloe, upland rice, *Opuntia humifusa* fruit, *Echinacea purpurea* and glutinous foxtail millet extracts, and this is a numerical value higher than 250 of retinoic acid, i.e., the control group.

Further, it can be seen from the individual extracts of Comparative Examples 1 to 5 that the aloe extract shows the highest hyaluronic acid production amount, and the *Opuntia humifusa* extract shows a hyaluronic acid production amount higher than those of other extracts. Further, it can be confirmed when Comparative Example 1, Example 1 and Example 2 are compared that a composite extract including an aloe extract and an upland rice extract has a higher effect in the hyaluronic acid production amount than an aloe extract alone, and the hyaluronic acid production amount is further remarkably increased when the *Opuntia humifusa* extract is additionally added to the composite extract including the aloe extract and the upland rice extract.

[Test Example 3-2] Confirming an Effect of Increasing Aquaporin3 (AQP3), i.e., a Moisturizing Factor After putting HaCaT cells into a 6-well plate, the HaCaT cells were attached to the 6-well plate for 18 hours. After replacing the 6-well plate with a serum-free DMEM, extracts prepared by above-mentioned Table 1 were treated in the serum-free DMEM to obtain cell samples. After treating the cell samples for 24 hours, removing a culture solution from each group of the cell samples, washing the culture solution-removed each group of the cell samples with PBS, and treating the cell samples with PBS which did not include drug that may affect protein quantification, low-temperature and room-temperature incubation processes were repeatedly performed to dissolve cells, and protein was collected from the dissolved cells. AQP3-ELISA kit (Elabscience Biotechnology Co., Ltd) was used in the quantification process, and the quantification process was progressed by a method provided by a manufacturer.

TABLE 4

|  | Treatment concentration (μg/mL) | Aquaporin3 production amount (%) |
|---|---|---|
| Untreated group | — | 100 |
| Comparative Example 1 | 100 | 174 ± 4.2 |
| Comparative Example 2 | 100 | 137 ± 2.8 |
| Comparative Example 3 | 100 | 156 ± 2.3 |
| Comparative Example 4 | 100 | 122 ± 1.7 |
| Comparative Example 5 | 100 | 134 ± 0.8 |
| Example 3 | 100 | 269 ± 2.3 |
| Example 7 | 100 | 235 ± 4.1 |
| Example 9 | 100 | 281 ± 2.9 |
| Example 10 | 100 | 279 ± 3.5 |
| Retinoic acid | 10 | 236 ± 0.6 |

As shown in the above-mentioned Table 4, an Aquaporin3 production amount, i.e., a moisturizing factor is higher in the groups treated with the individual extracts of Comparative Examples 1 to 5 and the composite extracts of Examples 3, 7, 9 and 10 than the untreated group.

Particularly, the Aquaporin3 production amount is 281 in the composite extract of Examples 9 including aloe, upland rice, *Opuntia humifusa* fruit, *Echinacea purpurea* and glutinous foxtail millet extracts, and this is a numerical value remarkably higher than 236 of retinoic acid, i.e., the control group.

Further, it can be seen from the individual extracts of Comparative Examples 1 to 5 that the aloe extract shows the highest Aquaporin3 production amount, and the *Opuntia humifusa* extract shows an Aquaporin3 production amount higher than those of other extracts. Further, it can be confirmed when Comparative Example 1, Example 1 and Example 2 are compared that a composite extract including an aloe extract and an upland rice extract has a higher effect in the Aquaporin3 production amount than an aloe extract alone, and the Aquaporin3 production amount is further increased when the *Opuntia humifusa* extract is additionally added to the composite extract including the aloe extract and the upland rice extract.

It can be confirmed from the hyaluronic acid and Aquaporin3 production amounts that the aloe extract as the individual extract shows remarkably high results, and efficacies of the hyaluronic acid and Aquaporin3 production amounts are remarkably increased in the composite extract obtained by mixing an individual extract with other extract of upland rice, *Opuntia humifusa*, *Echinacea purpurea* or glutinous foxtail millet compared to the individual extract alone.

[Test Example 4] Anti-Inflammatory Effect

[Test Example 4-1] Measuring Activities of Inhibiting Production of Nitrogen Monoxide (NO)

In order to confirm anti-inflammatory effects of the above-mentioned individual and composite extracts of the present invention, production inhibitory activities of nitric oxide (NO), i.e., one of inflammation causing materials were analyzed.

After putting RAW 264.7 cells into a 48-well plate, the RAW 264.7 cells were attached to the 48-well plate for 18 hours. After treating the RAW 264.7 cells with each of the composite extracts obtained in Preparation Example 2 along with 1 µg/mL of lipopolysaccharide (LPS), thereby inducing NO production of the treated RAW 264.7 cells, NO production inhibitory activities of the treated RAW 264.7 cells were analyzed through Griess reaction. The Griess reaction, as a method of quantitatively analyzing the amount of NO which was generated from cultured cells and discharged to a medium, comprised treating samples for 24 hours, dispensing 100 µl of a cell culture medium into a 96-well plate, mixing a Griess reaction solution A (a 1% sulfonyl amide solution dissolved in a 5% phosphoric acid solution) with a buffer solution B (0.1% naphtylethylenediamine dihydrochloride) at a ratio of 1:1 to dispense 100 µl of the mixture into each well of the 96-well plate, measuring absorbance values of cell samples at 540 nm from color changes due to NO production by using a multi-plate reader, and representing the measured absorbance values of the cell samples as average values of three repeated experiments.

TABLE 5

|  | Treatment concentration (µg/mL) | Nitric oxide (NO) production inhibition (%) |
|---|---|---|
| Comparative Example 1 | 100 | 64 ± 2.1 |
| Comparative Example 2 | 100 | 21 ± 6.8 |
| Comparative Example 3 | 100 | 14 ± 7.2 |
| Comparative Example 4 | 100 | 62 ± 1.6 |
| Comparative Example 5 | 100 | 75 ± 2.7 |
| Example 5 | 100 | 80 ± 1.9 |
| Example 7 | 100 | 81 ± 0.8 |
| Example 9 | 100 | 93 ± 3.1 |
| Example 10 | 100 | 95 ± 2.8 |
| 2-amino-4-methylpyridine | 10 | 92 ± 0.8 |

As shown in the above-mentioned Table 5, Examples 5, 7, 9 and 10, i.e., composite extracts according to the present invention have high NO production inhibition rates, i.e., inflammatory factors compared to Comparative Examples 1 to 5, i.e., individual extracts, and particularly, the composite extracts of Examples 9 and 10 including aloe, upland rice, *Opuntia humifusa* fruit, *Echinacea purpurea* and glutinous foxtail millet extracts have the highest NO production inhibition rates of 93 to 95%.

Among the individual extracts, Comparative Example 5, i.e., the glutinous foxtail millet extract has the highest NO production inhibition rate of 75%, and the aloe and *Echinacea purpurea* extracts each have NO production inhibition rates of 64% and 62% which are remarkably higher than the individual extract of the upland rice extract or *Opuntia humifusa* extract.

Further, it can be seen from Examples 5, 7, 9 and 10 that, although the upland rice extract or *Opuntia humifusa* extract which exhibits a low NO production inhibition rate is included as the individual extract, a composite extract including the upland rice extract and *Opuntia humifusa* extract has a more enhanced efficacy in the NO production inhibition rate.

[Test Example 4-2] Measuring Production Inhibitory Activities of Pro-Inflammatory Cytokines (TNF-α, IL-6, IL-1β)

In order to confirm anti-inflammation effects for the above-mentioned individual and composite extracts of the present invention, production inhibitory activities of pro-inflammatory cytokines (TNF-α: Tumor necrosis factor-α, IL-6: Interleukin-6, IL-1β: Interleukin-1β) were analyzed.

After putting RAW 264.7 cells into a 48-well plate, the RAW 264.7 cells were attached to the 48-well plate for 18 hours. After treating the RAW 264.7 cells with each of the composite extracts obtained in Preparation Example 2 along with 1 µg/mL of lipopolysaccharide (LPS), the treated RAW 264.7 cells were cultured for a predetermined time. After centrifuging culture mediums of samples at a rotational speed of 12,000 rpm for 3 minutes to obtain supernatants, pro-inflammatory cytokine production contents of the supernatants were measured. Before quantifying the samples, all of the samples were kept in a freezer at −20° C. The pro-inflammatory cytokines were quantified by using a mouse enzyme-linked immunosorbant assay (ELISA) kit (R&D Systems Inc., Minneapolis, Minn., USA), and r2 values of standard curves with respect to the standard were 0.99 or more.

TABLE 6

|  | Treatment concentration (µg/mL) | TNF-α production inhibition (%) | IL-6 production inhibition (%) | IL-1β production inhibition (%) |
|---|---|---|---|---|
| Comparative Example 1 | 100 | 24.3 ± 3.3 | 10.8 ± 1.8 | 22.8 ± 1.0 |
| Comparative Example 2 | 100 | ND | ND | ND |
| Comparative Example 3 | 100 | ND | 5.9 ± 3.5 | ND |
| Comparative Example 4 | 100 | 48.8 ± 0.5 | 56.7 ± 1.6 | 42.2 ± 1.6 |
| Comparative Example 5 | 100 | 45.5 ± 1.2 | 60.1 ± 1.2 | 39.4 ± 3.8 |
| Example 5 | 100 | 57.8 ± 2.3 | 71.2 ± 1.1 | 50.6 ± 1.4 |
| Example 7 | 100 | 69.4 ± 3.1 | 71.3 ± 3.0 | 64.3 ± 0.9 |
| Example 8 | 100 | 65.4 ± 3.1 | 73.3 ± 3.0 | 68.3 ± 0.9 |
| Example 9 | 100 | 71.3 ± 0.8 | 87.3 ± 0.9 | 67.8 ± 1.7 |
| Example 10 | 100 | 75.3 ± 2.8 | 86.1 ± 0.9 | 70.8 ± 2.8 |

As shown in the above-mentioned Table 6, Examples 5, and 7 to 10, i.e., composite extracts according to the present invention have high pro-inflammatory cytokine production inhibition rates compared to Comparative Examples 1 to 5, i.e., individual extracts.

Further, it can be seen from Examples 5, and 7 to 10 that, although the upland rice extract of Comparative Example 2 or *Opuntia humifusa* extract of Comparative Example 3 which exhibits a very low or no pro-inflammatory cytokine production inhibition rate is included as the individual extract, a composite extract including the upland rice extract and *Opuntia humifusa* extract has a more enhanced efficacy in the pro-inflammatory cytokine production inhibition rate.

[Test Example 5] Measuring Production Inhibitory Activities TARC and MDC, i.e., Atopic Factors In order to confirm atopy alleviating effects for the above-mentioned individual and composite extracts of the present invention, atopic chemokine (TARC: Thymus and activation regulated chemokine, MDC: Macrophage-derived chemokine) production inhibitory activities were analyzed.

After putting HaCaT cells into a 24-well plate, the HaCaT cells were attached to the 24-well plate for 18 hours. After treating the HaCaT cells with samples of Examples 5, 7, 9 and 10 along with 10 ng/mL of interferon-γ (IFN-γ), the treated HaCaT cells were cultured for a predetermined time. After centrifuging culture mediums of the samples at a rotational speed of 12,000 rpm for 3 minutes to obtain supernatants, atopic chemokine production contents of the supernatants were measured. Before quantifying the samples, all of the samples were kept in a freezer at −20° C. The TARC and MDC contents were quantified by using a human enzyme-linked immunosorbant assay (ELISA) kit (R&D Systems Inc., Minneapolis, Minn., USA), and r2 values of standard curves with respect to the standard were 0.99 or more.

TABLE 7

|  | Treatment concentration (μg/mL) | TARC production inhibition (%) | MDC production inhibition (%) |
| --- | --- | --- | --- |
| Comparative Example 1 | 100 | 12.3 ± 3.4 | 10.8 ± 1.8 |
| Comparative Example 2 | 100 | ND | ND |
| Comparative Example 3 | 100 | ND | ND |
| Comparative Example 4 | 100 | 45.5 ± 3.1 | 51.2 ± 1.1 |
| Comparative Example 5 | 100 | 4.5 ± 3.2 | 12.1 ± 1.6 |
| Example 5 | 100 | 50.2 ± 3.8 | 52.9 ± 0.5 |
| Example 7 | 100 | 56.8 ± 0.9 | 59.7 ± 2.7 |
| Example 9 | 100 | 61.3 ± 2.6 | 68.7 ± 1.2 |
| Example 10 | 100 | 65.3 ± 2.2 | 73.5 ± 3.2 |
| Silymarin | 10 | 58.1 ± 4.3 | 60.2 ± 1.4 |

As shown in the above-mentioned Table 7, Examples 5, 7, 9 and 10, i.e., composite extracts according to the present invention have high atopic chemokine production inhibition rates compared to Comparative Examples 1 to 5, i.e., individual extracts, and particularly, the composite extracts of Examples 9 and 10 including aloe, upland rice, *Opuntia humifusa* fruit, *Echinacea purpurea* and glutinous foxtail millet extracts have the highest atopic chemokine production inhibition rates.

Further, it can be seen from Examples 5, 7, 9 and 10 that, although the upland rice extract of Comparative Example 2 or *Opuntia humifusa* extract of Comparative Example 3 which exhibits a very low or no atopic chemokine production inhibition rate is included as the individual extract, a composite extract including the upland rice extract and *Opuntia humifusa* extract has a more enhanced efficacy in the atopic chemokine production inhibition rate.

[Formulation Example 1] Manufacturing a Softening Tonic

As shown in the following Table 8, a softening tonic comprising a composite extract as an active ingredient was manufactured by a common method.

TABLE 8

| Mixture ingredients | Content (wt %) |
| --- | --- |
| Example 1 | 0.5 |
| Butylene glycol | 2.0 |
| Propylene glycol | 2.0 |
| Acrylate/C10-C30 alkyl acrylate crosspolymer | 0.1 |
| Polysorbate 80 | 0.4 |
| Argininic acid | 0.1 |
| Xanthan gum | 0.1 |
| Hyaluronic acid | 1.0 |
| Preservative, pigment, perfume | Appropriate amount |
| Purified water | Up to 100 |

[Formulation Example 2] Manufacturing a Cream

As shown in the following Table 9, a cream comprising a composite extract as an active ingredient was manufactured by a common method.

TABLE 9

| Mixture ingredients | Content (wt %) |
| --- | --- |
| Example 5 | 0.5 |
| Beta-1,3-glucan | 5.0 |
| Polysorbate 80 | 1.5 |
| Squalane | 5.0 |
| Glycerin | 5.0 |
| Butylene glycol | 3.0 |
| Propylene glycol | 3.0 |
| Cetearyl olivate/sorbitan olivate | 1.0 |
| Preservative, pigment, perfume | Appropriate amount |
| Purified water | Up to 100 |

[Formulation Example 3] Manufacturing a Skin External Application Agent

As shown in the following Table 10, a skin external application agent comprising a composite extract as an active ingredient was manufactured by a common method.

TABLE 10

| Mixture ingredients | Content (wt %) |
| --- | --- |
| Example 9 | 0.5 |
| Beta-1,3-glucan | 5.0 |
| Polysorbate 80 | 5.0 |
| PEG 60 | 2.0 |
| Shea butter | 5.0 |
| Squalane | 5.0 |
| Glycerin | 10.0 |
| Propylene glycol | 10.0 |
| Cetearyl olivate/sorbitan olivate | 1.0 |
| Preservative, pigment, perfume | Appropriate amount |
| Purified water | Up to 100 |

The above-described description is only for an illustrative description of the present invention, and a skilled person in the art may understand that the present invention can be realized as an altered formation within the scope of the substance of the present invention. Therefore, the disclosed embodiments and experimental examples should be considered in a descriptive sense only and not for purposes of limitation. The scope of the invention is defined not by the aforementioned description of the present invention but by the appended claims, and all differences within the scope will be construed as being included in the present invention.

INDUSTRIAL APPLICABILITY

Cosmetic and pharmaceutical compositions according to the present invention can be diversely used in beauty care, pharmaceutical and cosmetic product fields for the purposes of prevention, alleviation and treatment of skin diseases since the cosmetic and pharmaceutical compositions are excellent in moisturizing effects, anti-inflammatory effects and atopy alleviating effects.

The invention claimed is:

1. An emulsion consisting essentially of at least 5 mg of an aloe extract, at least 5 mg of an upland rice extract, at least 5 mg of an *Opuntia humifusa* extract, at least 5 mg of an *Echinacea* purpurea extract, and at least 5 mg of a glutinous foxtail millet extract.

* * * * *